United States Patent [19]

White et al.

[11] Patent Number: 5,059,527

[45] Date of Patent: Oct. 22, 1991

[54] DETECTION OF ENDOTOXINS OF GRAM NEGATIVE BACTERIA

[76] Inventors: David C. White, 11104 Poplar Ridge Rd., Knoxville, Tenn. 37932-1925; Marc W. Mittelman, 12909 Old Stage Rd., Knoxville, Tenn. 37922

[21] Appl. No.: 448,071

[22] Filed: Dec. 8, 1989

[51] Int. Cl.$^5$ .............................................. C12Q 1/02
[52] U.S. Cl. ........................................ 435/29; 435/34
[58] Field of Search ................................... 435/29, 34

[56] References Cited

U.S. PATENT DOCUMENTS

| | | | |
|---|---|---|---|
| 3,365,271 | 1/1968 | Abel et al. | 435/34 X |
| 3,891,508 | 6/1975 | Merrick | 435/34 |
| 4,093,381 | 6/1978 | Karamian | 435/38 X |
| 4,107,077 | 8/1978 | Sullivan, Jr. et al. | 435/38 X |
| 4,195,225 | 3/1980 | Karamian | 250/373 |
| 4,224,031 | 9/1980 | Mee et al. | 435/71 X |
| 4,276,050 | 6/1981 | Firca et al. | 436/825 X |
| 4,279,774 | 7/1981 | Lindsay et al. | 435/38 X |
| 4,376,634 | 3/1983 | Prior et al. | 436/502 |
| 4,434,237 | 2/1984 | Dinarello | 436/542 |
| 4,503,149 | 3/1985 | Boyd | 435/39 X |
| 4,606,824 | 8/1986 | Chu et al. | 210/635 |
| 4,683,196 | 7/1987 | McLaughlin | 435/810 X |
| 4,755,459 | 7/1988 | Pearson et al. | 435/34 X |
| 4,758,509 | 7/1988 | Ottley | 435/34 X |
| 4,803,162 | 2/1989 | Smith et al. | 435/34 X |
| 4,812,409 | 3/1989 | Babb et al. | 435/38 X |

OTHER PUBLICATIONS

Zykin et al.–Chem. Abst. vol. 110 (1989), p. 91502u.
Bone et al.–Chem. Abst. vol. 105 (1986), p. 110,029k.
Edlund et al.–Chem. Abst. vol. 103 (1985), p. 156,969d.
Sensitive Assay, Based on Hydroxy Fatty Acids from Lipopolysaccharide Lipid A, for Gram-Negative Bacteria in Sediments–Parker, et al., App. & Envir. Microbio. Nov. 1982, pp. 1170–1177.
Proceedings of the 1986 U.S. Army Chemical Research Development and Engineering Center Scientific Conference on Chemical Defense Research Prepared by M. D. Rausa, Jun. 1989, CRDEC-SP-87008.
Determination of Microbial Fatty Acid Profiles at Femtomolar levels in Human Urine and the Initial Marine Microfouling Community by Capillary Gas Chromatography–Chemical Ionization Mass Spectrometry with Negative Ion Detection Odham, et al., J. of Microbio. Methods 3 (1985) pp. 331–344.
Surface Carbohydrates of the Prokaryoric Cell, Chapter 4, pp. 114–116, edited by I. Sutherland, 1977.

*Primary Examiner*—Sam Rosen
*Attorney, Agent, or Firm*—Michael A. Mann

[57] ABSTRACT

A method and apparatus for inferring and quantifying the presence and identifying endotoxins of Gram-negative bacteria in a bacteria-containing sample comprising obtaining a sample, extracting any lipids from the sample using supercritical $CO_2$, hydrolyzing the lipid insoluble residue with a mild acid catalyst, derivatizing the hydroxy fatty acids, and analyzing the sample using a gas chromatograph and mass spectrometer. The results of the gas chromatograph and mass spectrometer analysis allow detection of as few as 10 bacteria or parts of bacteria in a 100 ml sample and specification of the type of Gram-negative bacterial group.

25 Claims, 2 Drawing Sheets

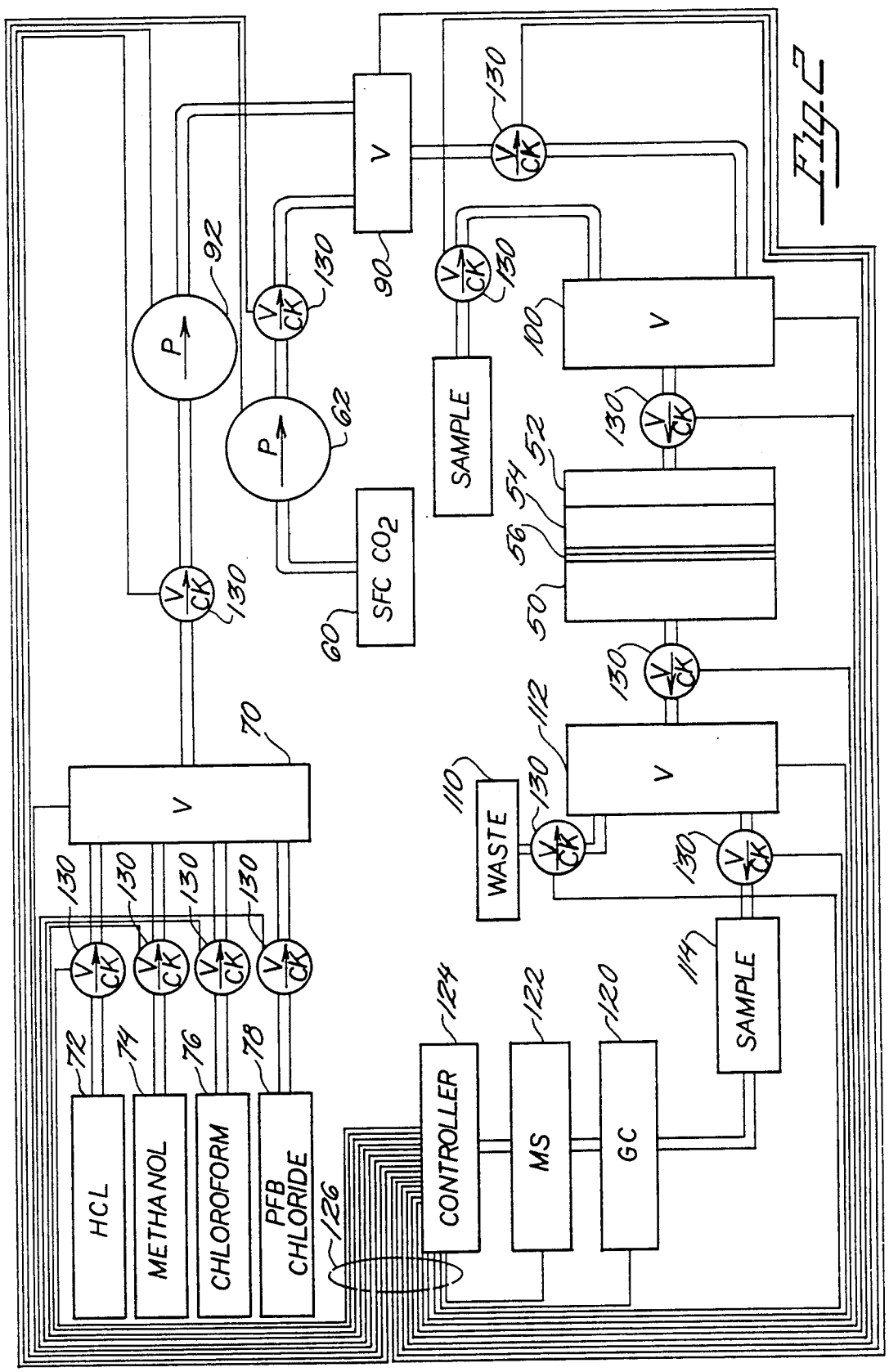

DETECTION OF ENDOTOXINS OF GRAM NEGATIVE BACTERIA

BACKGROUND OF THE INVENTION

1. Field of the Invention

The present invention relates to detecting the presence of endotoxins of Gram-negative bacteria in solid, liquid and gaseous samples. More specifically, the present invention is a method and apparatus for automatically and accurately infering the presence and type of Gram-negative bacterial endotoxins from solid, liquid and gaseous samples by measuring hydroxy fatty acid methyl esters of Lipid A lipopolysaccharides.

2. Background of the Invention

Pathogenic microorganisms are bacteria responding negatively to the Gram stain, hence the designation Gram-negative bacteria. The presence of Gram-negative bacteria stimulates a host of responses by the immune system of human beings. In particular, these bacteria are pyrogenic or fever producing. Endotoxic bacteria can also induce other responses including abortions, pulmonary edema, hemorrhagic pneumonia, uremia, anaphylactic shock, and death of the host body. Endotoxins can enter the body through the air or by injection and even slight traces of endotoxins provoke a response.

Part of the problem of avoiding exposure of humans to pathogenic bacteria is solved by being able to detect the presence of pathogenic organisms among nonpathogenic organisms. Fortunately, not only does their virulence distinguish them but also their biomolecular makeup. Scientists have looked to cellular lipids, in particular, for distinguishing microorganisms and have found that these lipids are distinctive not only of the genus but the species. Since lipids of Gram-negative bacteria are characteristic, identification of the lipid is tantamount to identifying the bacteria from which it came. This critical piece of information could greatly accelerate tracing the cause of an infection and thus hasten the treatment of the disease.

Within the cellular lipids of cells are cholesterol, triglycerides, phospholipids, quinones and lipopolysaccharides. The last of these, lipopolysaccharides or LPS, which are exclusively major components of Gram-negative bacterial cell walls, contain covalently bound hydroxy fatty acid lipids. The analysis of LPS hydroxy fatty acids, provides the sensitivity and selectivity needed for accurate identification. LPS, which contains the endotoxic constituents of Gram-negative bacteria, comprise a covalently linked lipid A component and a polysaccharide component, the latter being a chain of covalently linked monomeric units which form a large carbohydrate. The lipid A component of the LPS (which is thought to be responsible for the observed physiological reactions to endotoxins) will be used as a distinguishing biomolecule. Other cells, including fungi, protozoa, and other bacteria can be distinguished by the approximately 200 different types of extractible (without prior hydrolysis) phospholipid fatty acids, the most commonly used biomarkers.

The detection of covalently bound hydroxy fatty acid in the LPS provides definitive identification of Gram negative LPS lipid A endotoxins. This specificity allows classification to the family and in some cases species level amongst Gram-negative bacteria.

It is important that certain environments be as Gram-negative-bacteria-free as possible. For example, Gram-negative bacteria are the most common contaminants of water. Also, intravenous fluids, parenteral fluids, prostheses, artificial organs, organs for transplant, medical and veterinary procedure devices, eye and ear care products, foods, potable water, and water used in fabrication of semiconductors must be exceptionally free of bacteria before use. These environments must also be free of endotoxins, which can exist in the absence of viable bacterial cells.

Methods for identifying the presence and type of bacteria in general are not new. Biochemical techniques have been applied to assess microbial biomass in different environments. Some of these techniques require culturing of the organisms or quantitative removal of organisms from the sample and some do not. Procaryotic biomass, for example, can be accurately estimated from the quantity of muramic acid if the proportions of cyanophytes, Gram-negative and Gram-positive bacteria are known. These proportions can be determined by examining the cell wall with an electron microscope or by biochemical markers.

There are several methods used for detecting Gram-negative bacteria. In one, a sample is subjected to chloroform-methanol extraction (the so-called Bligh-Dyer extraction method). The lipid soluble fraction is subjected to mild alkaline methanolysis, then fractionated into polar lipid, glycolipid, and neutral lipid fractions via silicic acid chromatography. The polar lipid fraction, which contains the unique signature biomarkers, phospholipids, is then analyzed via capillary column gas chromatography. While bacterial identification to the species level is possible with this technique, endotoxins are not specifically detected.

Another test for the presence of Gram-negative bacteria is the rabbit pyrogen test, described more fully in U.S. Pat. No. 4,093,381, in which a rabbit is exposed to a potentially endotoxic sample and its body temperature monitored. This test is relatively insensitive, detecting about $5 \times 10^{-8}$ grams LPS or 500,000 bacteria per milliliter, and is nonspecific; that is, it cannot distinguish between bacterial and nonbacterial pyrogens. Furthermore, this test is slow and expensive and the increasing concern for animal welfare raises ethical issues.

A third test for the presence of gram negative bacteria is the Limulus Amebocyte Lysate (LAL) test which uses an extract of the horseshoe crab. This method, described in U.S. Pat. No. 4,279,774, is relatively more sensitive than the rabbit pyrogen test, detecting about $10^{-11}$ grams LPS or about 1000 to 10,000 bacteria per milliliter. This test is subject to interferences when applied to fluids that contain proteins such as insulin, growth hormone, blood and urine, and is difficult to execute. A LAL test can be performed by three methods. They are the so-called clot assay, the chromogenic assay, and the kinetic assay. It, like the rabbit pyrogen test, is nonspecific in detecting endotoxin-producing bacteria, is costly and again raises the ethical issues associated with animal testing.

Other methods for detecting endotoxins are described in U.S. Pat. Nos. 4,758,509, 4,276,050, 4,195,225, 3,891,508, and 3,365,277.

There is a need for a fast method and apparatus for determining the presence and type of endotoxic LPS of Gram-negative bacteria with a high degree of accuracy and speed.

SUMMARY OF THE INVENTION

According to its major aspects, the present method isolates, quantifies and identifies hydroxy-fatty acids derived from Lipid A lipopolysaccharide present in a bacterial sample to determine the presence of endotoxins of Gram-negative bacteria. Any LPS present in the sample is concentrated then extracted and purified through a series of steps, until its hydroxy fatty acids methyl esters (OHFA-ME) can be derivatized and identified by comparison to known references. The present method includes filtration to concentrate whole bacteria and parts of bacteria in a sample, extraction of contaminating lipids present in the sample; hydrolysis, purification, and derivatization of the LPS; separation of the OHFA-ME via gas chromatography; then detection, quantitation, and identification of the OHFA-ME using a mass spectrometer. Derive means to obtain one compound from another. In particular, derivatization involves redistributing the electrical charge of the polar groups of the molecule and raising the molecular vapor pressure, with the result that the derived compounds are volatile, an essential requirement for use in gas chromatography. Derivatization is a standard procedure with gas chromatography.

It is a feature of the present invention that supercritical carbon dioxide with modifiers is used as a solvent for extracting the lipids. Supercritical carbon dioxide is nonhazardous and has strong solvating properties since solvent strength is related to density, viscosity and diffusivity. It has a low critical temperature and its polarity can be varied by the addition of modifiers.

It is another feature of the present invention that both bound and unbound LPS are extracted so that the measurement can be much more sensitive for a given sample. The present method is capable of detecting as few as ten cells or cell fragments and of identifying the groups of bacteria by comparing the patterns of different OHFA-ME of the sample with that of reference bacteria.

It is another feature of the present invention that the mass spectrograph uses negative ion detection for improved sensitivities, sensitivities down to $10^{-17}$ moles or the equivalent of 10 to 100 bacteria or $10^{-12}$ grams LPS. Also this feature has the advantage of allowing differentiation between bacterial groups at very low concentrations. This feature can be of especial advantage in tracing the source of endotoxin contamination.

It is a feature of the present invention that the method and apparatus are capable of being automated for convenience and speed in obtaining results and for on-line monitoring of products.

Still other advantages of the present invention are that it does not use animals for testing and is relatively free of environmental factors and interferences by other molecules similar to LPS.

BRIEF DESCRIPTION OF THE DRAWINGS

In the drawings:

FIG. 2 is a system diagram of the equipment used according to the present invention.

DETAILED DESCRIPTION OF A PREFERRED EMBODIMENT

Figure 1:
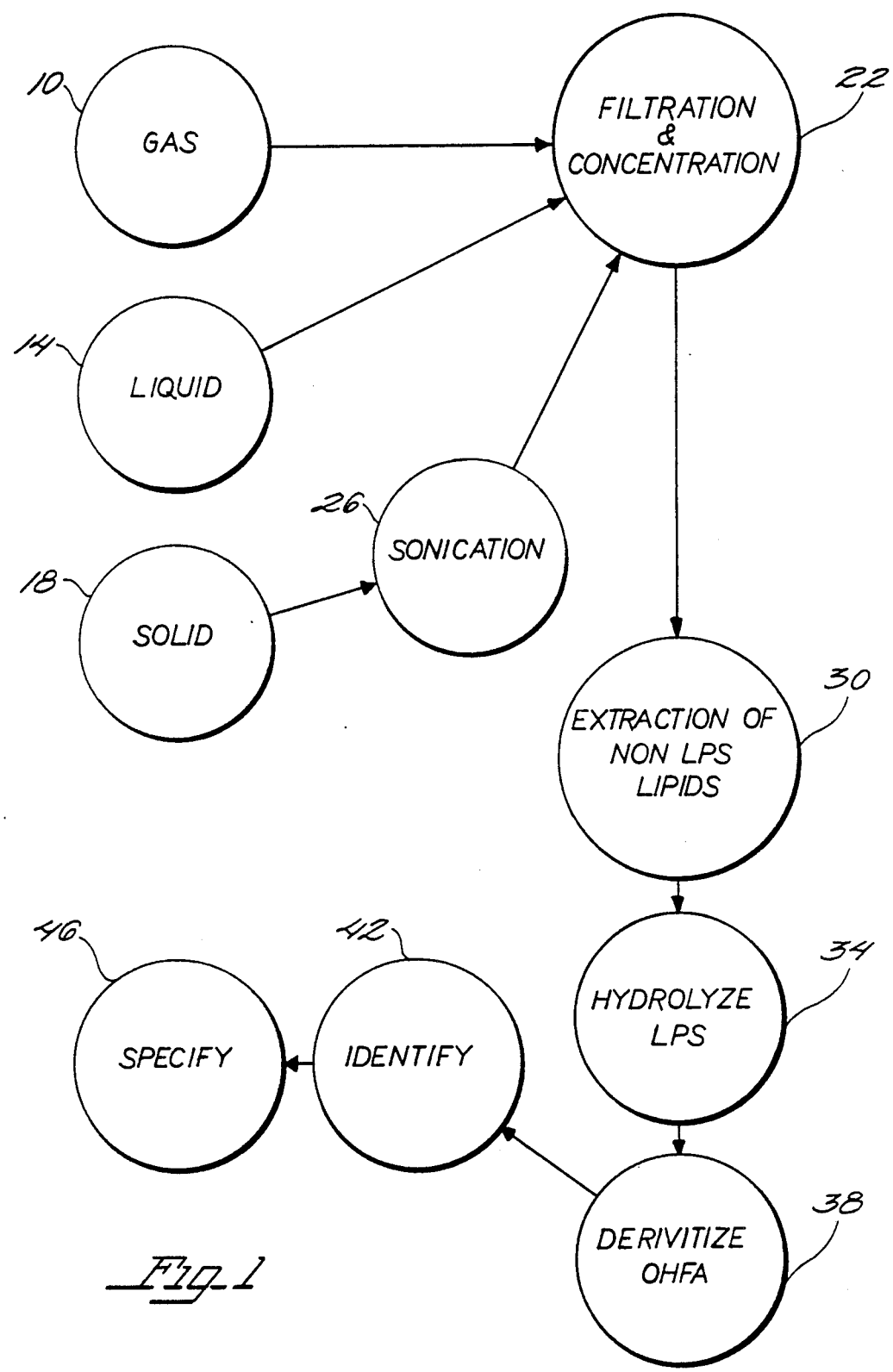
FIG. 1 is a flow chart of the method according the present invention.

The present invention is a method and apparatus for detecting the presence of endotoxins of Gram-negative bacteria and inferring the specific type of Gram-negative bacteria by an accurate measurement of hydroxy fatty acids of lipid A lipopolysaccharides (LPS) in a sample. The method has four basic steps: (1) sample recovery and concentration, (2) extraction and purification, (3) derivatization and separation, and (4) detection and analysis.

Lipids, such as the lipid portion of LPS, are generally insoluble in water because they contain fatty acids, which are long-chain aliphatic carboxylic acids, such as stearic acid or myristic acid. The non LPS lipids can be readily extracted from the insoluble LPS lipid A. Specific hydroxy fatty acids are covalently linked to the polysaccharide portion of the LPS via an ester or amide linkage. This linkage must be broken by acid hydrolysis, using a strong acid, before the OHFA can be extracted from the lipid extracted residue. Once the ester or amide linkage is broken, one can separate the fatty acid, which is nonpolar, from the rest of the LPS, which is polar, by an extraction process, in which these polar and nonpolar components are partitioned between aqueous (polar) and generally organic (nonpolar) solvents. The separated hydroxy fatty acids can then be collected and identified.

Referring now to FIG. 1, the bacteria sample may be obtained originally from a gas 10 such as air, a liquid 14 such as water, or a solid 18 such as soil or from any other solid, liquid, or gaseous matrix where Gram-negative bacteria may be present, such as on a heart valve. A liquid or gaseous sample may be passed through a filter directly, a solid sample may be dissolved or washed with pyrogenic endotoxin-free water before filtration and concentration 22.

The size of the sample does not have to be large. For example, a liquid sample may be obtained by filtering only 100 milliliters or so through a 0.2 micron filter, ion exchange resin, charge-modified membrane, polyurethane foam, glass fibers, or polycarbonate filters. Solid objects may be washed and undergo sonication 26 and the rinse water collected and filtered as described above for gases 10 and liquids 14. Air samples can be pulled through a filter coated with a polymer to trap and concentrate volatile compounds. The goal of filtration and concentration 22 is to obtain bound (to the bacteria) and unbound LPS.

The resulting sample will thus contain whole bacteria and parts of bacteria. The contaminating lipids can now be separated from the other bacterial components by an extraction step 30. The sample is suspended in an aqueous solution, a nonpolar (generally organic) solvent is added and the mixture is shaken. The nonpolar solvent is an organic solvent such as supercritical sulfur hexafluoride with methanol or supercritical carbon dioxide and methanol, although a one-phase organic solvent system such as chloroform/methanol/water, or hexane/isopropanol would also be appropriate. The lipid insoluble residue contains proteins, nucleic acids, carbohydrates and LPS if any.

Supercritical carbon dioxide has many advantages over other nonpolar solvents. The "supercritical" designation indicates that carbon dioxide ($CO_2$) is in a phase in which it would not be found at ordinary temperatures and pressures; at room temperature and atmospheric pressure, it is a gas. At increased pressure, and at an appropriate temperature, carbon dioxide will liquify.

Liquid, or "supercritical" carbon dioxide or, alternatively, sulfur hexafluoride, is an exceptional, nonpolar extraction solvent. It has exceptional solvating properties since its viscosity and diffusion coefficients are rather like those of a gas in that it demonstrates good penetrating power and speed, but its density is rather like that of a liquid. It is inexpensive, nontoxic, and nonflammable; and it reaches supercriticality (liquification) easily. In contrast, many nonpolar, organic solvents are toxic or flammable. Supercritical $CO_2$ may be modified to increase polarity to the extent required for the extraction by adding such solvent modifiers as methanol and/or methylating agents.

Since the LPS will be in the aqueous layer of this extraction, the nonpolar layer is discarded. The ester and amide linkages that connect the fatty acids (including the OHFA) to the remainder of the LPS are then broken via an acid-catalyzed hydrolysis 34 involving a strong, inorganic acid, preferably hydrochloric acid (HCl). Hydrolysis is followed by the esterification of the free carboxylic acid portion of the fatty acids using a mixture of HCl and methanol ($CH_3OH$), preferably a HCl/supercritical $CO_2$/$CH_3OH$ mixture to produce fatty acid methyl esters.

Fatty acid methyl esters (including the OHFA methyl esters) can be separated from this reaction mixture by second extraction process.

The fatty acid methyl esters will be analyzed by capillary gas chromatography and identified by mass spectrometry. Capillary gas chromatography involves eluting a vaporized sample through a long, thin tube containing a solid support using a carrier gas such as helium. Because different compounds bind to the solid support more strongly than others, it takes varying lenghts of time for the carrier gas to elute compounds through the solid support. Given the correct set of operating conditions for the gas chromatograph, each different compound will reach the detector at a different time, generating a signal that can be used to identify its presence.

In order to make the OHFA methyl esters more volatile, and thus easier to elute, they are derivatized 38 using a halogenated hydrocarbon, preferably pentafluorobenzoyl (PFB) chloride or heptafluorobutyryl (HFB) chloride.

If the capillary gas chromatograph feeds directly into a mass spectrometer, each fatty acid can be analyzed by mass spectrometry as soon as it is eluted. A mass spectrometer bombards a compound with high energy electrons, generating a set of ions of differing masses that create a signal pattern called a spectrum which can be used for identification 42 of any OHFA in the original bacterial sample and specification 46 of the type of bacterial group by comparison with the spectra of reference compounds.

Alternatively, the bacterial sample can be derivatized before extraction by methylating with a methylating agent such as trimethylphenylammonium hydroxide. Pre-extraction derivatization can remove ester-linked but not amide-linked LPS. Although sensitivity would be reduced, resolution in the analysis by the gas chromatograph-mass spectrometer sequence would be increased.

Referring to FIG. 2, the heart of the system is the extraction cylinder 50 such as manufactured by Keystone Scientific Part number 65510 for use as an SFE reservoir includes a frit filter 52 and a charged membrane 54, or foam filter, on a stainless steel support 56. Into cylinder 50 is directed extracting compounds, preferably supercritical $CO_2$ from a $CO_2$ tank 60 pumped by a supercritical fluid pump 62. A motorized valve 70 selects from tanks containing hydrolyzing, derivatizing and purifying agents: namely HCl 72, Methanol 74, Chloroform 76, and PFB chloride 78. The agents are selectively transferred to mixing valve 90 by a high performance liquid chromatography (HPLC) pump 92. Mixing valve 90 mixes methanol and chloroform with supercritical $CO_2$ and injects it to three way valve 100. Mixing valve 90 is a high pressure valve, such as that made by High Pressure Valve Co. for direct, alternatively, supercritical $CO_2$, PFB chloride, chloroform, HCl and methanol to the extraction cylinder.

The bacterial sample is selected by an autosampler 102 and fed into three way valve 100 for injection to cylinder 50. Outside cylinder 50, wastes are directed to waste tanks 110 by valve 112 and OHFA methyl ester samples transferred to sampler vials in another autosampler 114, such as those manufactured by Hewlett Packard for analysis with a gas chromatograph. The samples are run through a capillary gas chromatograph 120, preferably of a type similar to that manufactured by Hewlett Packard Capillary Gas Chromatograph 5850 Series II and then to a mass spectrograph 122 such as that made by VG-Trio-1 or a Finnigan ion trap mass spectrometer and the results analyzed received by a controller 124 having a built in data analyzer such as a Hewlett Packard HP-3365 programmed to read the results of the mass spectrograph and compare the results with reference data. Controller 124 controls all valves and pumps, preferably electrically by cabling 126 so that the process can be automatically sequenced and safeguards built in through programming of the controller. Each liquid transfer line contains an in-line check valve 130 to prevent back flow of fluids or samples.

An example of the method of the present invention is provided.

EXAMPLE OF THE PROCESS TO RECOVER LPS-LIPID A HYDROXY FATTY ACIDS

Tests were performed using 1-10 mg of lyophilized bacteria (*Escherichia coli, Bacillus cereus*, and the algae *Chlorella vulgaris*). The sample was placed on a stainless steel frit in a Millipore filter holder or a Keystone supercritical fluid extractor. One side of the apparatus was connected to 1/16th in stainless steel tubing and a high pressure valve to a 250 mL Isco syringe pump which was in turn connected to a source of supercritical grade carbon dioxide in an aluminum tank. Modifiers were added through high pressure valves using Waters's high pressure piston pumps. The other end of the extraction apparatus was connected to 10-20 cm lengths of 20-50 micrometer diameter fused silica tubing as a pressure reduction system with a graphite/polyimide ferrule to maintain the supercritical conditions in a flowing system. The effluent was collected in glass bottles at the end of the reduction system (the expanding gas cools the vessels and the recovery is quantitative). The assessment of extraction efficiency was determined by injecting the recovered material on a capillary gas chromatograph/quadrupole mass spectrometer (Hewlett Packard 5995) and comparing to one-phase extractions of the bacteria and algae with the chloroform/methanol/water system (Bligh and Dyer) followed by silicic acid fractionation of the lipids into neutral, glyco, and polar lipids and derivatization and analysis with the gas chromatograph/mass spectrometer. Exposure for 10 min at a pressure ranging from 140 to 400 atm, at 100 C. yielded 90% of the neutral lipid fatty acids. Increasing the polarity of the extraction by adding 20% methanol, or sulfur hexafluoride with 10% methanol resulted in the release of between 20 and 96% of the polar (phospholipid) fatty acids with a 10 minute extraction at 400 atm and 100 degrees C. Addition of derivatizing agents such as treatment with 3:1 methanol/toluene with 0.1M fresh KOH (at 80 degrees C.) or trimethylphenylammonium hydroxide in methanol followed by extraction by supercritical carbon dioxide allowed recoveries of 77-88% of the polar lipid fatty acids. None of these procedures affected the proportions of the different fatty acids. Three successive re-extractons with either the polar extractants or the pre-derivatized material resulted in no additional fatty acids in the last treatment. There was no evidence of damage to cyclopropane or unsaturated fatty acids. The extracted residue of $E.$ $coli$ which contains no hydroxy fatty acids in the extractable lipids, when treated with approximately 10% 0.1N methanolic hydrochloric acid in supercritical carbon dioxide resulted in recovery of the LPS hydroxy fatty acids.

It will be obvious many changes and modifications of the present method and apparatus may be made by someone skilled in the art without departing from the spirit and scope of the invention which is defined by the following claims.

What is claimed is:

1. A method for identifying and quantifying endotoxins of Gram-negative bacteria in a bacteria-containing sample comprising the steps of:
   extracting any lipids in said sample to obtain a lipid insoluble residue;
   hydrolyzing any hydroxy fatty acids in said lipid insoluble residue;
   derivatizing said hydroxy fatty acids; and
   detecting said derivatized hydroxy fatty acids; said extracting is done with a supercritical solvent.

2. The method of claim 1 wherein said extracting is done with an inorganic supercritical solvent.

3. The method of claim 2 wherein said inorganic supercritical solvent is supercritical $CO_2$.

4. The method of claim 1 where in said detecting of said derivatized hydroxy fatty acids is done by a capillary gas chromatograph, mass spectrometer sequence.

5. The method of claim 4 wherein said extracting is done with an inorganic supercritical solvent.

6. The method of claim 5 wherein said inorganic supercritical solvent is supercritical $CO_2$.

7. The method of claim 4 wherein said extracting is done with an inorganic solvent.

8. The method of claim 7 wherein said solvent is $CO_2$.

9. A method for identifying and quantifying endotoxins of Gram-negative bacteria in a bacteria-containing sample comprising the steps of:
   extracting any lipids with an inorganic supercritical solvent to leave a lipid insoluble residue;
   hydrolyzing said lipid insoluble residue using an inorganic acid catalyst to break any amide or ester linkages in any lipopolysaccharides present in said lipid insoluble residue to form a hydrolized product;
   derivatizing said hydrolized product with a halogenated hydrocarbon; and
   transferring said derivatized hydrolized product to a means for detecting said hydrolized derivatized product.

10. The method of claim 9 wherein said inorganic solvent is $CO_2$.

11. The method of claim 9 wherein said acid catalyst is HCl.

12. The method of claim 10 wherein said acid catalyst is HCl.

13. The method of claim 9 further comprising the step of methylating said sample prior to said extracting step.

14. The method of claim 13 wherein said methylating is by trimethylphenylammonium hydroxide.

15. The method of claim 9 wherein said halogenated hydrocarbon is selected from the group consisting of pentafluorobenzoyl chloride and heptafluorobutyryl chloride.

16. The method of claim 10 wherein said halogenated hydrocarbon is selected from the group consisting of pentafluorobenzoyl chloride and heptafluorobutyryl chloride.

17. The method of claim 11 wherein said halogenated hydrocarbon is selected from the group consisting of pentafluorobenzoyl chloride and heptafluorobutyryl chloride.

18. The method of claim 12 wherein said halogenated hydrocarbon is selected from the group consisting of pentafluorobenzoyl chloride and heptafluorobutyryl chloride.

19. The method of claim 9 wherein said means for analyzing said hydroxy fatty acids is a capillary gas chromatograph and a mass spectrometer.

20. The method of claim 10 wherein said means for analyzing said hydroxy fatty acids is a capillary gas chromatograph and a mass spectrometer.

21. The method of claim 11 wherein said means for analyzing said hydroxy fatty acids is a capillary gas chromatograph and a mass spectrometer.

22. The method of claim 12 wherein said means for analyzing said hydroxy fatty acids is a capillary gas chromatograph and a mass spectrometer.

23. The method of claim 13 wherein said means for analyzing said hydroxy fatty acids is a capillary gas chromatograph and a mass spectrometer.

24. The method of claim 14 wherein said means for analyzing said hydroxy fatty acids is a capillary gas chromatograph and a mass spectrometer.

25. The method of claim 15 wherein said means for analyzing said hydroxy fatty acids is a capillary gas chromatograph and a mass spectrometer.

* * * * *